(12) United States Patent
Moisio et al.

(10) Patent No.: US 7,152,457 B2
(45) Date of Patent: Dec. 26, 2006

(54) IMPACTOR A FRAME PART FOR AN IMPACTOR A PART TO BE USED IN AN IMPACTOR AND A METHOD FOR PROCESSING ELEMENTS BELONGING TO THE IMPACTOR

(75) Inventors: Mikko Moisio, Tampere (FI); Risco Luoma, Tampere (FI); Kimmo Pietarinen, Tampere (FI); Leo Holma, Kangasala (FI); Marko Palonen, Tampere (FI)

(73) Assignee: Dekati Oy, Tampere (FI)

( * ) Notice: Subject to any disclaimer, the term of this patent is extended or adjusted under 35 U.S.C. 154(b) by 0 days.

(21) Appl. No.: 10/496,084

(22) PCT Filed: Nov. 20, 2002

(86) PCT No.: PCT/FI02/00923

§ 371 (c)(1),
(2), (4) Date: Nov. 22, 2004

(87) PCT Pub. No.: WO03/044491

PCT Pub. Date: May 30, 2003

(65) Prior Publication Data

US 2005/0081600 A1 Apr. 21, 2005

(30) Foreign Application Priority Data

Nov. 21, 2001 (FI) .................................. 20012258

(51) Int. Cl.
*G01M 7/00* (2006.01)
*G01N 3/00* (2006.01)
*G01N 3/31* (2006.01)
*G01N 3/303* (2006.01)
*G01N 3/313* (2006.01)
*G01N 3/17* (2006.01)
*G01N 3/307* (2006.01)

(52) U.S. Cl. ..................................................... 73/12.09
(58) Field of Classification Search ............... 73/865.5, 73/12.09
See application file for complete search history.

(56) References Cited

U.S. PATENT DOCUMENTS

| | | | | |
|---|---|---|---|---|
| 4,133,202 A | * | 1/1979 | Marple | 73/28 |
| 4,264,343 A | * | 4/1981 | Natarajan et al. | 55/126 |
| 6,401,553 B1 | * | 6/2002 | Keskinen et al. | 73/865.5 |
| 6,431,014 B1 | * | 8/2002 | Liu et al. | 73/863.22 |
| 6,647,758 B1 | * | 11/2003 | Marple et al. | 73/28.03 |
| 6,889,591 B1 | * | 5/2005 | Sabates et al. | 89/1.1 |
| 2001/0013244 A1 | | 8/2001 | Marple et al. | |
| 2004/0025567 A1 | * | 2/2004 | Marjamaki et al. | 73/28.05 |

FOREIGN PATENT DOCUMENTS

SU 894482 A 10/1981

* cited by examiner

*Primary Examiner*—Edward Lefkowitz
*Assistant Examiner*—Octavia Davis
(74) *Attorney, Agent, or Firm*—Venable LLP; Eric J. Franklin

(57) ABSTRACT

An impactor, a frame part for an impactor, a part to be used in an impactor, and a method for processing elements belonging to the impactor. Different elements belonging to different stages of the impactor are coupled to each other with a connecting element in such a way that they can be inserted in the frame part of the impactor, removed from it, or processed, as a single unit.

16 Claims, 5 Drawing Sheets

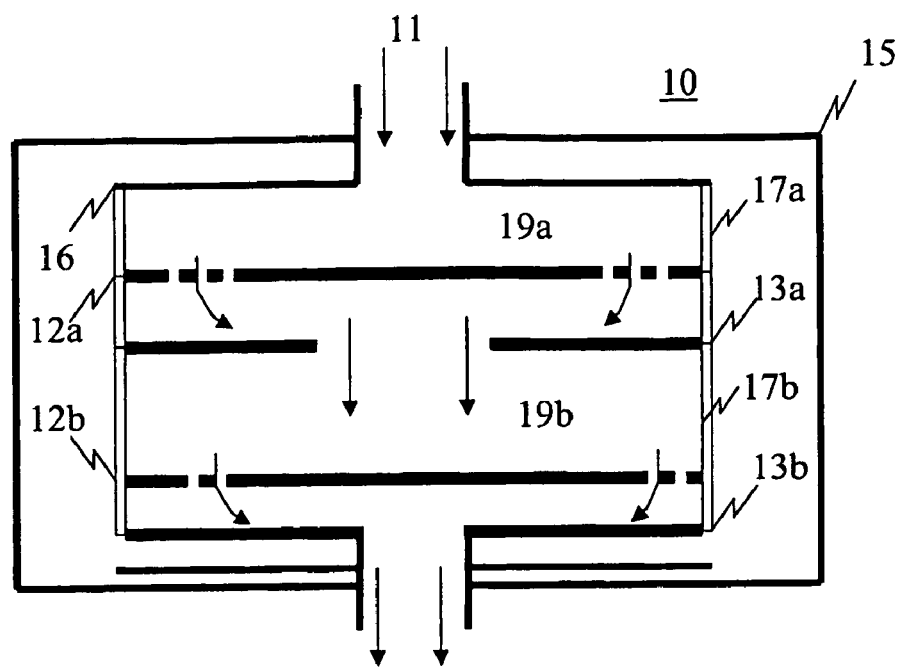
Fig. 1 *(Prior art)*
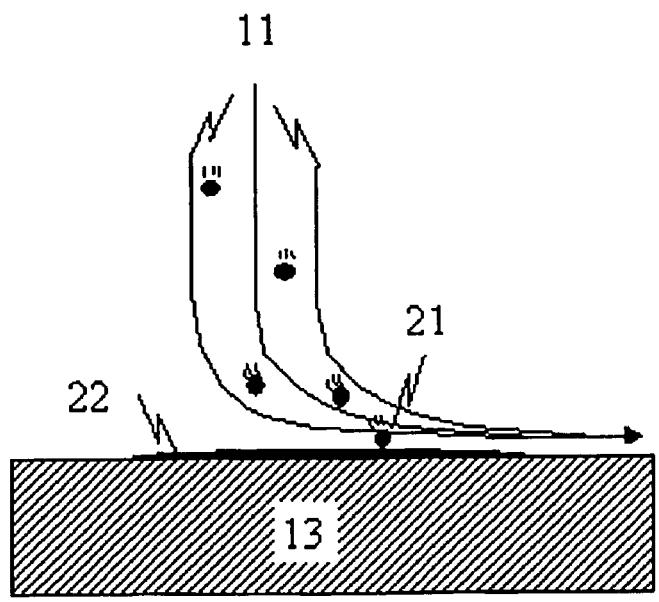
Fig. 2 *(Prior art)*

IMPACTOR A FRAME PART FOR AN IMPACTOR A PART TO BE USED IN AN IMPACTOR AND A METHOD FOR PROCESSING ELEMENTS BELONGING TO THE IMPACTOR

CROSS-REFERENCE TO RELATED APPLICATIONS

The present invention claims priority from Finnish patent application 20012258 filed 21 Nov. 2001 and is the U.S. National Phase under 35 U.S.C. §371 of PCT/FI2002/00923 filed 20 Nov. 2002.

FIELD OF THE INVENTION

The invention relates to an impactor, a frame part for an impactor, a part to be used in an impactor, and to a method for processing elements belonging to an impactor.

BACKGROUND OF THE INVENTION

With tightening environmental regulations, there is an increasing need for the measurement of particle emissions. In particular, the need for measurement is present in the development of filtering methods, in the research of various combustion processes, as well as in processes for monitoring actual emissions. In particle measurements, so-called cascade impactors have been conventionally used to classify the particles according to the particle size.

FIG. 1 shows a cross-sectional view of an impactor 10 consisting of several stages according to prior art. To simplify the figure, only the first two stages have been drawn. The flow 11 to be analyzed is sucked, for example by negative pressure, through the impactor 10. The air flow 11 is introduced through the frame structure 15 of the impactor to a first chamber 19a. Each stage comprises a nozzle part 12a; 12b equipped with orifices which are passed through by the flow carrying particles. Collection surfaces 13a; 13b are placed behind the nozzle parts 12a; 12b. The collection surface is provided with at least one outlet, through which the flow is allowed to flow to the next chamber or out of the impactor.

FIG. 2 shows a detail of the collection surface 13. The flow direction of the air flow 11 through the orifices of-the nozzle part is abruptly changed when it impacts upon the collection surface 13. Particles 21 carried by the flow 11 and having a sufficiently low mechanical mobility cannot follow the abrupt change in the direction of the flow but they hit the collection surface 13. The particles 21 having hit the collection surface 13 are deposited on the collection surface 13, forming a mass 22.

The mechanical mobility of the particles depends in a known way on the particle size. This makes it possible to classify the particles selectively according to the size. By selecting, in a known way, the number and size of orifices in the nozzle part 12a, 12b shown in FIG. 1, the distance between the nozzle part 12a; 12b and the collection surface 13a; 13b, as well as the flow rate to be used, it is possible to dimension each impactor stage in such a way that only particles having a mechanical mobility smaller than a desired value, i.e. being larger than a given particle size, are deposited on the collection surface 13a; 13b at each stage.

The successive stages can be dimensioned so that the first stage collects the largest particles (for example, particles with a diameter greater than 100 μm), the second stage collects the particles slightly smaller than these (for example, 10 to 100 μm), and the next stages would collect smaller and smaller particles, respectively. Thus, by measuring the masses 22 deposited on the collection surfaces 13 at the different collecting stages, it is possible to determine the size distribution of the particles in the flow under analysis. In conventional impactors, the mass deposited on the collection surface 13 is measured by weighing. In electrical impactors, an estimate of the mass deposited on the collection surface is made by monitoring the current caused by electric charges discharged by particles deposited on the collection surface.

A problem with the above-described impactor of prior art is the amount of work required for removing and reinstalling the collection surfaces. As mentioned earlier, in conventional impactors it is necessary to remove the collection surfaces for weighing; however, in electrical impactors it is also necessary to remove the collection surfaces, although not for obtaining the measurement result itself, as in conventional impactors. After a given measuring time, both impactor types require cleaning to remove the mass deposited on the collection surfaces. If this were not done, the collection surfaces would eventually be filled in such a way that the mass deposited on them would either impair the passage of the flow or, when disengaged, it would be carried to the next stage and cause an error in the measurements. To reduce this "blow off" effect, as well as the bouncing of particles hitting the collection surface, the collection surface 13 is typically treated with a substance which facilitates adhesion.

Both conventional and electrical impactors must be cleaned at regular intervals. Impactors of prior art are constructed in such a way that they must be disassembled part by part. For example, to disassemble the impactor of FIG. 1, first the shielding cover 15 would be removed, then the cover part 16 of the first stage and the supporting/shielding part 17a underneath the cover. Next, the nozzle part 12a of the first stage can be removed. After the removal of the nozzle part, it is possible to remove the collection surface 13a. After this, the supporting/shielding part 17b, the nozzle part 12b and the collection surface 13b of the second stage can be removed, respectively. In a corresponding manner, all the stages of the impactor are gone through. After the disassembly, the removed collection surfaces 13a, 13b can be weighed, if necessary. The partly disassembled impactor can then be cleaned, for example by placing the parts in a separate washing device. After the cleaning, the impactor is assembled in an order inverse to that presented above, after which the impactor can be used for measuring again.

SUMMARY OF THE INVENTION

As presented above, it is necessary to clean the impactor. However, the disassembly and assembly of the impactor of prior art is a relatively complex and laborious operation. It is an aim of the impactor and the parts intended for use in the impactor, and the processing method, to eliminate the above-described problems of prior art. By means of the invention, it is possible to remove or install all the collection surfaces in the impactor in a single operation, if necessary.

By means of a part according to the invention, the impactor can also be cleaned in a simpler and faster way than according to the prior art.

BRIEF DESCRIPTION OF THE DRAWINGS

In the following, the invention will be described in detail with reference to the appended drawings, in which FIG. 1 shows an impactor of prior art, FIG. 2 shows the impingement of particles to be measured on a collection surface.

DETAILED DESCRIPTION OF THE INVENTION

FIGS. 1 and 2 have been discussed above in connection with the prior art.

Figure 3:
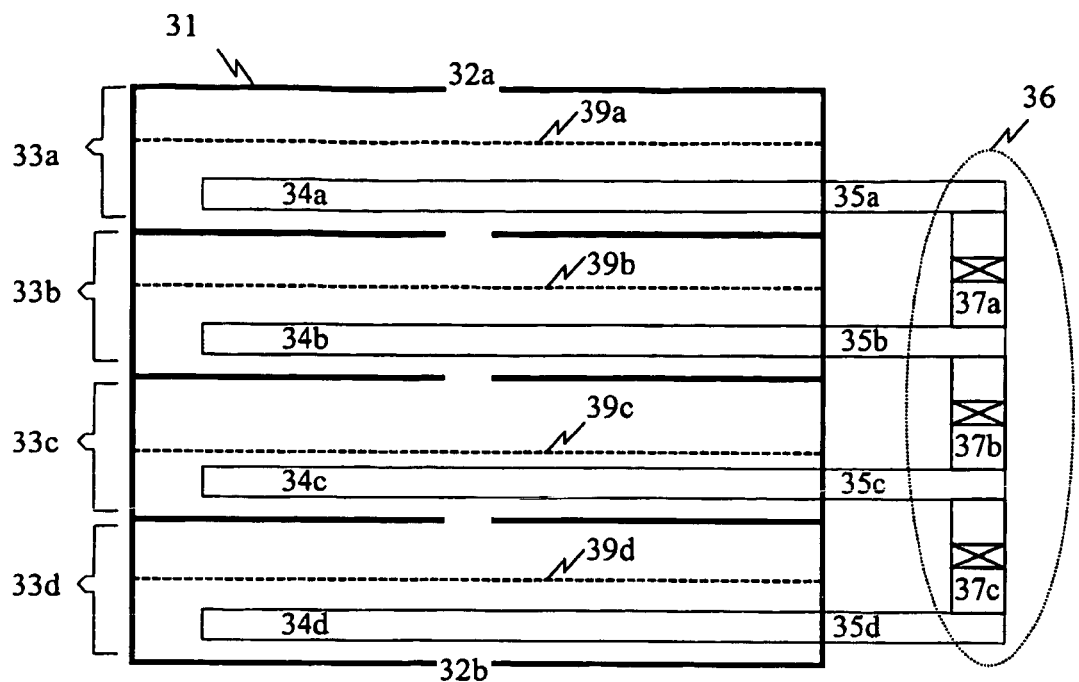
FIG. 3 illustrates an embodiment of the impactor and a part to be used in the impactor according to the invention.

FIG. 3 shows an embodiment of the impactor according to the invention in a cross-sectional view. The impactor consists of a frame part 31 with an inlet connector 32a for supplying a flow to be analyzed into the impactor, and an outlet connector 32b for discharging the measured flow from the impactor. To simplify the drawing, only four stages 33a14 33d are shown in FIG. 3, but it will be obvious for a person skilled in the art that the number of stages in the impactor may vary to a great extent. In view of the arrangement according to the invention, the number of stages in the impactor is not significant as long as it is greater than one. Each stage is preferably provided with a separate nozzle part 39a–39d to provide the desired flow properties.

Furthermore, each stage is provided with a separate collection surface 34a–34d, on which the particles in the flow under analysis are deposited, as described above. The shape of the collection surfaces is mainly dependent on the need for measurement. In some measurements, it is advantageous to use cylindrical collection surfaces, in other cases rectangular ones. The arrangement according to the invention does not limit the geometry used in the collection surfaces, wherein it can be selected according to the respective need.

Each collection surface 34a–34d is coupled to a supporting means 35a–35d. Preferably, the supporting means 35a–35d are integrated with respect to the collection surfaces 34a–34d to avoid tolerances caused by extra connections which will complicate the placement of the collection surfaces 34a–34d precisely in the correct position in relation to the other parts of the stages 33a–33d, such as the nozzle parts 39a–39d. The placement of the collection surface in the correct position in relation to the other parts of the stage is important, because the dimensioning of the stage is a factor determining which particles are deposited in each stage, as was stated above in the description of the prior art. If the collection surface is in an incorrect position, it may cause significant errors in the measurement results of the impactor.

In an advantageous embodiment, both the collection surface 34a–34d and the supporting means 35a–35d are formed by a cylindrical object, for example a metal tube, inserted in the frame part 31 of the impactor. In view of the operation of the impactor, it is advantageous to seal the connection points of the frame part 31 and the supporting means 35a–35d in such a way that the flow to be analyzed cannot be affected by an undesirable outflow or inflow caused by the through hole. This sealing can be implemented in a way known as such by a person skilled in the art. The supporting means 35a–35d may also have a more complex structure; i.e., they may consist of, for example, several parts. Furthermore, the arrangement according to the invention does not restrict the position of the collection surface in relation to the through hole, although the figures show, as an advantageous embodiment of the arrangement, an example in which the collection surface is aligned with the through hole and the supporting means 35a–35d.

In FIG. 3, the supporting means 35a–35d are coupled to each other with a connecting element 36 outside the frame part 31. The connecting element 36 may be a single solid part, to which the supporting means 35a–35d are coupled, or the connecting element 36 may consist, as shown in FIG. 3, of several smaller coupling units 37a–37c which preferably couple the supporting parts 35a–35d connected to the collecting surfaces of adjacent stages to each other. The advantage of the solid connecting element 36 is its simplicity and easy manufacture. In view of the control of the device, in turn, it is more advantageous to use several coupling units, because the coupling units can be preferably provided with control means, e.g. a millimetre screw, by means of which it is possible to adjust the position of the supporting means coupled to each other and thereby also the collection surfaces coupled to the supporting means, in relation to each other and the frame part. This is advantageous for the adjustment of the impactor.

The connecting element 36 connects the supporting means 35a–35d and the collection surfaces 34a–35d further coupled to them to form a single aggregate, which will be called a combination element in this application, in such a way that said aggregate can be separated as a single unit from the frame part. Thus, preferably all the collection plates belonging to the different stages 33a–33d of the impactor can be removed at one time. This provides an obvious advantage to the arrangement of prior art, because the removal and the installation of all the different collection stages can thus be performed in a single operation and does not require that the whole impactor is disassembled into small parts. In a corresponding manner, also the installation of the collection surfaces in the impactor can be implemented in a single operation.

On the other hand, the connecting element 36 can be made such that all the collection stages do not need to be removed together, if desired. For example, the coupling units 37a–37c can be made such that, if necessary, the coupling units 37a and 37b can be removed from the supporting means 35b connected to the collection surface 34b of the second stage 33b in such a way that the collection surface 34b can be removed from the frame part 31 without a need to remove the collection surfaces of the other stages, or the supporting means coupled to them, from the frame part 31.

The combination element can be preferably implemented in such a way that some of the elements connected to it, such as the collection surfaces, can be replaced in a single operation. This is achieved, for example, by connecting the collection surfaces to the supporting means in such a way that they can be easily removed, if desired. This makes it possible to replace and change collection surfaces by removing at least some of the collection surfaces of the combination element, for example, by means of a separate element, and by installing new collection surfaces respectively, several collection surfaces at a time. In an advantageous embodiment, after the measurement, the combination elements are removed from the frame part of the impactor and inserted into a separate collecting part comprising a separate compartment for the collection surface of each stage. After this, all the collection surfaces are removed in a single operation in such a way that they remain in their respective compartments within the collecting part. This is preferably achieved by providing the combination element with a separate locking means, by which all the collection plates are released or locked against the supporting means, respectively.

After the removal of old collection surfaces, the combination element is cleaned and the new collection surfaces are installed from a part for inserting collection surfaces, provided with a separate compartment for each new collection surface. The combination element is inserted in the inserting part in such a way that each supporting means is connected to the respective collection surface. In this way, all the collection surfaces can be installed in a single operation and it will not be necessary to install each collection surface separately as in the arrangement of prior art.

Figure 4:
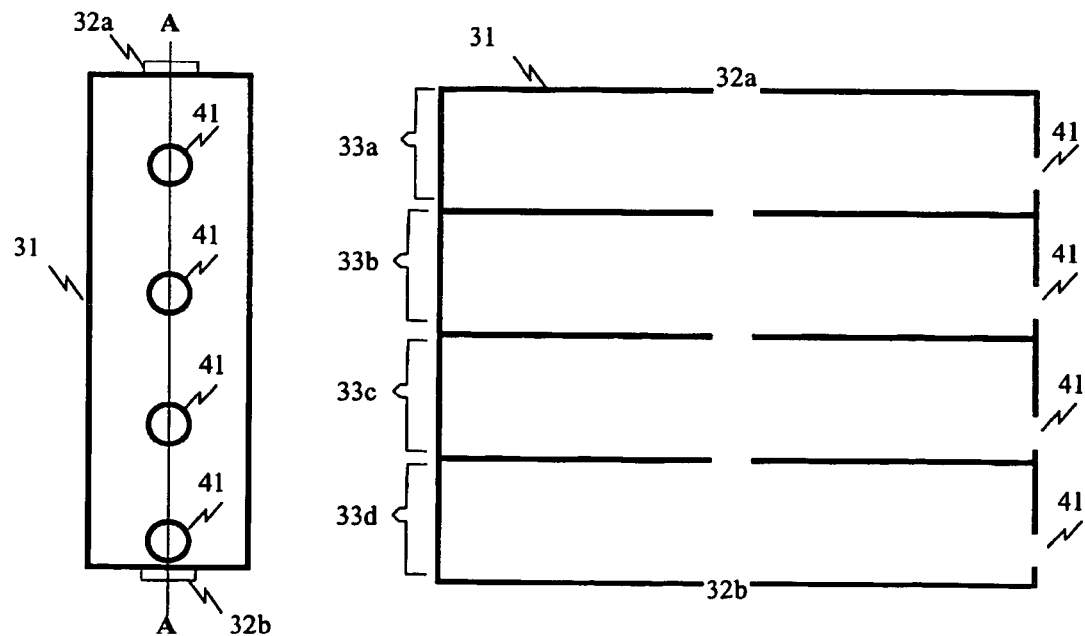
FIG. 4 illustrates an embodiment of a frame part for the impactor according to the invention.

FIG. 4 shows a frame part 31 for an impactor according to the invention, as well as a cross-sectional view along the line A—A of the frame part. The frame part 31 is provided with lead-through provisions, for example by drilling holes 41 in the frame part 31. These through holes make it possible to insert various elements in the frame part 31. Such elements may include, for example, the above-described collection surfaces 34a–34d, cleaning means to be described below, or nozzle parts. The invention makes it possible to provide an arrangement, in which the frame part 31 may, if necessary, consist of a single piece, because the insertion or removal of the elements does not require the disassembly of the frame part. Naturally, the frame part may also consist of several pieces, wherein the advantage of the invention is clearly manifested. The elements can be handled and adjusted without a need to disassemble the impactor.

Figure 5:
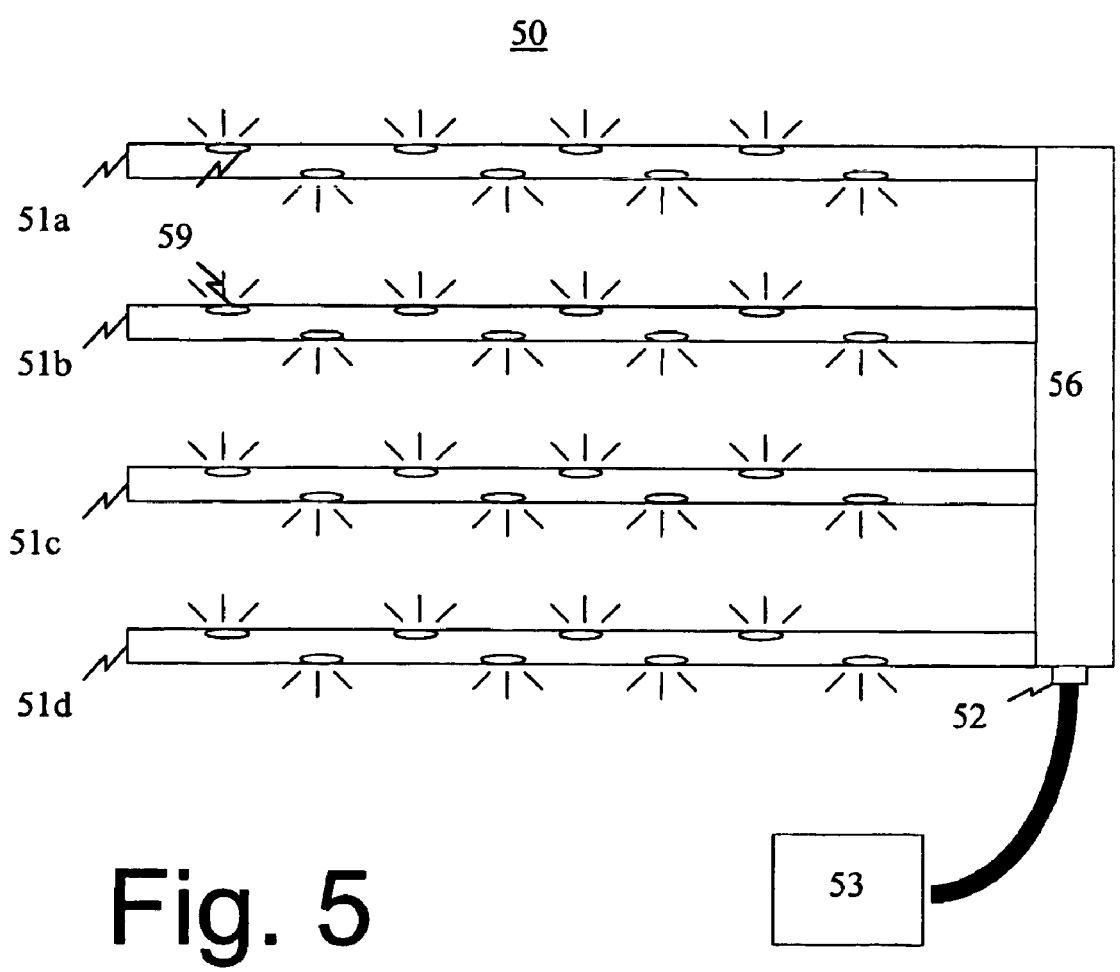
FIG. 5 shows an embodiment of a part to be used for cleaning the impactor according to the invention.

FIG. 5 shows an auxiliary device 50 according to the invention, intended to be used in connection with the impactor for its cleaning. The device 50 comprises nozzle parts 51a–51d to be inserted in the frame part 31, provided with holes 59 to introduce a substance used for cleaning, preferably hot water vapour, into the frame. The basic structure of the device corresponds to the structure already presented above in connection with FIG. 3; that is, the device comprises a connecting element 56, by means of which nozzle parts 51a–51d intended for several different stages can be inserted in the frame part 31 or removed from it as a single unit.

The device 50 is also provided with a connector 52 for feeding a substance to be used for cleaning, from a source 53 to the device 50. The dispensing of the substance inside the device 50, from the connector 52 to the nozzle parts 51a–51d, can be implemented in a way known as such for a person skilled in the art.

Figure 6:
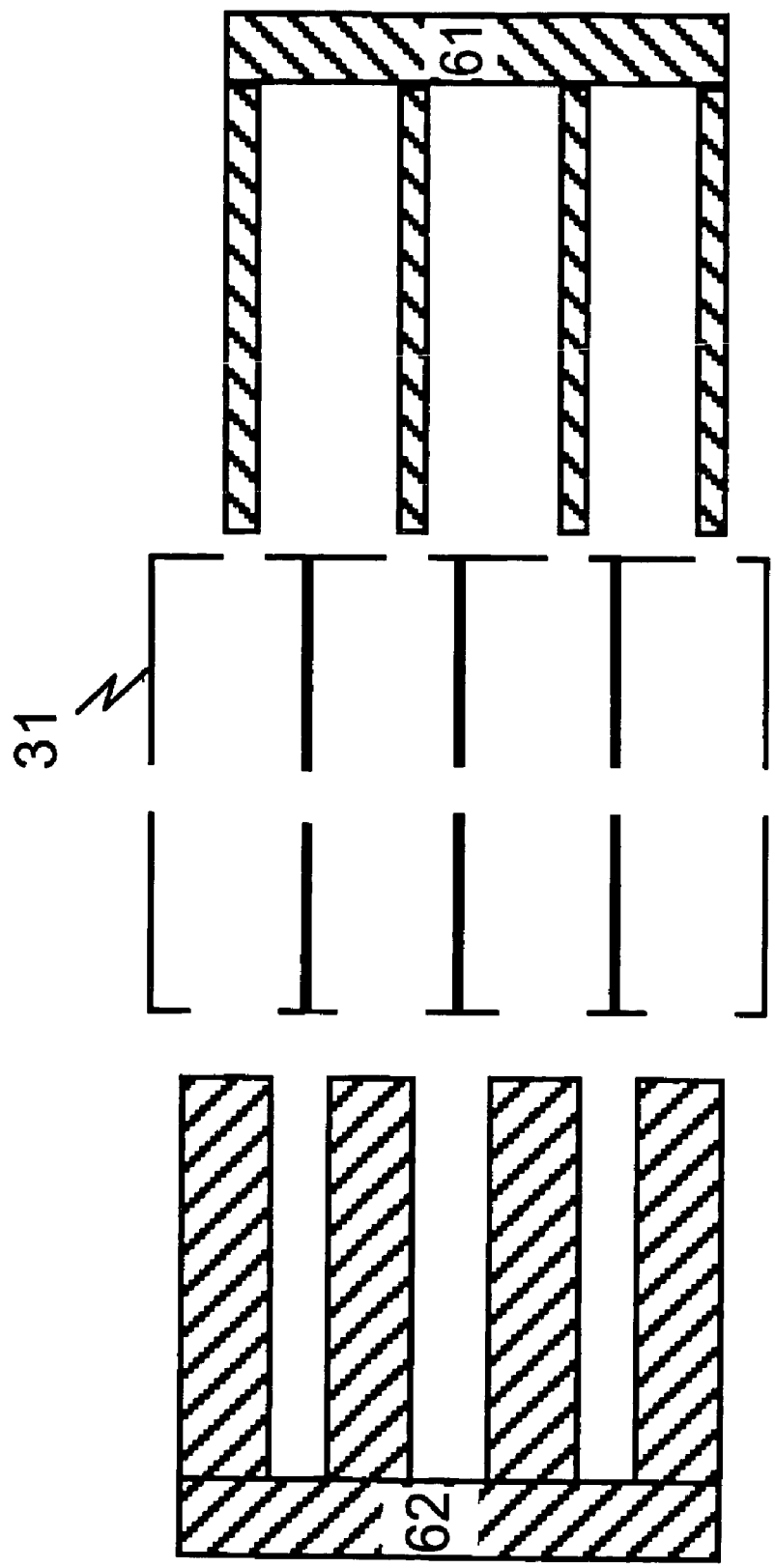
FIG. 6 shows a second embodiment of the impactor and two parts to be used in the impactor according to the invention.

FIG. 6 shows a second advantageous embodiment of the above-described basic arrangement according to the invention. In addition to the element 61 connecting the collection surfaces of the different stages, as described above in connection with FIG. 3, and the frame part 31, a second combination element 62 is also shown in FIG. 6. The basic structure of the second combination element 62 is similar to that of the first combination element 61 with the difference that the second combination element does not comprise the collection surfaces of the stages but, for example, the nozzle parts of the different stages and/or other parts needed in the structures of the stages. Preferably, the structure of the second combination element may be such that it comprises all the elements needed in the stage, except for the collection surfaces.

Figure 7:
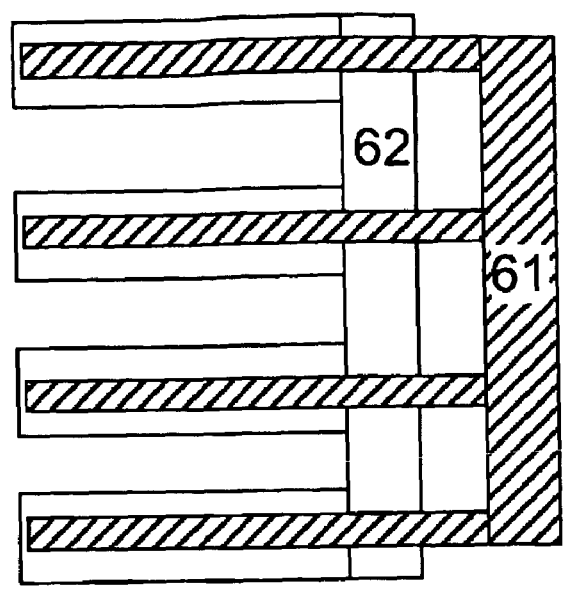
FIG. 7 shows a third embodiment of a part to be used in the impactor according to the invention.

If the structure of the impactor according to the invention is implemented according to FIG. 6, in which the first and the second combination elements 61 and 62 are inserted into the frame part from opposite sides, the frame part 31 must naturally be provided with two sets of through holes, one for the first combination element 61 and the other for the second combination element 62. The structure can also be implemented in such a way that both the combination elements are inserted from the same side, wherein the alternatives are to make two sets of through holes on the same side or to install both of the combination elements in the same through holes. The latter alternative could be implemented, for example, in such a way that the second combination element 62 is first installed in its position, after which the first combination element 61 is inserted in the second combination element 62, as shown in FIG. 7. It will be obvious for a person skilled in the art that the mutual order of connecting the first and second combination elements 61 and 62, as well as the order of connecting them in the frame part, can also be different from that presented above. For example, the first combination element 61 can be connected to the second combination element 62 first, after which the unit thus formed is inserted in the frame part 31.

The above-described elements, intended for use in the impactor, can be preferably processed by the following method, which belongs to the scope of the same inventive idea as the above-described impactor, frame part for the impactor, and parts intended for use in the impactor. In the method, the part to be used in the impactor, comprising elements intended for different stages of the impactor, preferably collection surfaces or nozzle parts, are processed in such a way that at least some of the different elements are processed simultaneously in different processes.

Figure 8:
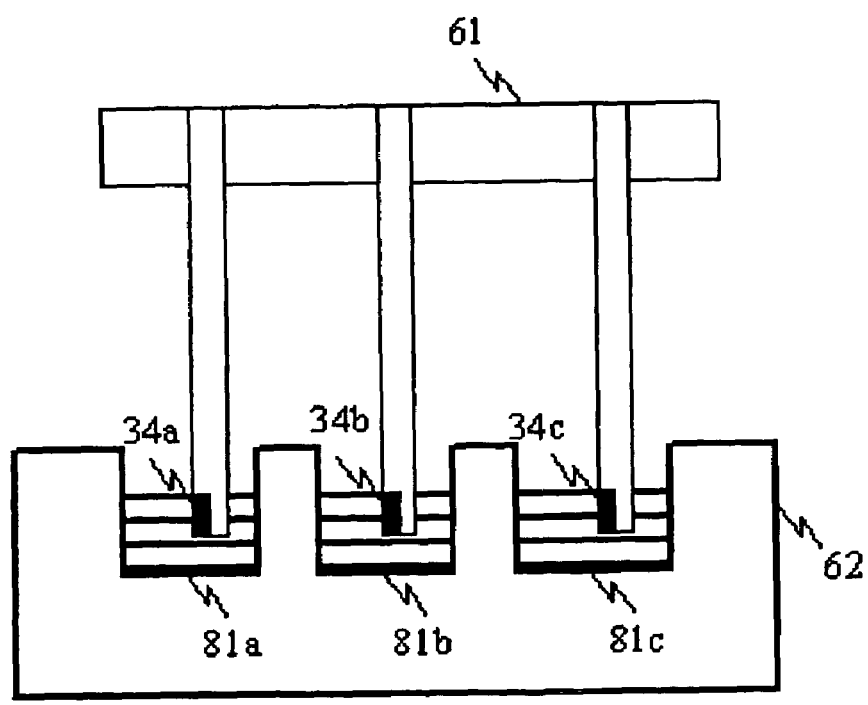
FIG. 8 shows an embodiment of the processing method according to the invention.

FIG. 8 shows an embodiment of the method according to the invention. In FIG. 8, the combination element 61 is inserted in a cleaning part 80 which comprises a separate cleaning solution 81a–81c for each collection surface 34a–34c. The collection surfaces 34a–34c are fixed to the combination element 61, wherein a single operation will be sufficient to set them for processing. Because each collection surface 34a–34c is provided with a separate cleaning solution, cleaning liquids of different concentrations can be used for different collection surfaces simultaneously. This makes it possible, for example, to subject the most soiled collection surfaces to stronger cleaning processes, preferably a stronger cleaning solution, than the less soiled collection surfaces, without operations involved in the removal of the surfaces.

In addition to the above-described cleaning process, the method is also suitable for other processing related to the combination element, such as, for example, the coating of the elements, greasing, or other processes to reduce undesirable effects.

Hereinabove, some embodiments of the impactor and the parts to be used in the impactor according to the invention have been described in detail; however, the invention is not restricted solely to these embodiments, but it may vary within the scope of the appended claims. In particular, the term impactor must not be interpreted as a restriction to any given impactor type. The basic idea of the invention will work as long as the impactor comprises more than one stage. Thus, it will be obvious for a person skilled in the art that the invention can be utilized in, but is not restricted solely to, for example, cascade impactors, electrical impactors, such as electrical low pressure impactors, or virtual impactors.

The invention claimed is:

1. An electrical impactor, comprising:
   at least two impactor stages, each stage comprising a nozzle part and a collection surface and a support to which at least one of the collection surface or the nozzle part is operatively connected;
   a connecting element operatively connected to the support; and
   a frame part enclosing the at least two impactor stages, wherein said connecting element is arranged such that at least one element one of the nozzle part or the collection surface can be introduced in and/or removed from said impactor stages arranged in the frame part as a single unit.

2. The impactor according to claim 1, wherein said nozzle part is used for cleaning the impactor stage.

3. The impactor according to claim 1, wherein said connecting element comprises at least one coupling unit.

4. The impactor according to claim 3, wherein said coupling unit allows the adjustment of a single element without affecting the other elements coupled to said connecting element.

5. The impactor according to claim 4, wherein said coupling unit allows the removal of one of the nozzle part or the collection surface from said frame part or its insertion in said frame part without affecting other elements coupled to said connecting element.

6. A frame part for an electrical impactor comprising several stages, wherein said frame part enclosing the at least two impactor stages includes holes for allowing the insertion of at least two elements belonging to different stages in said frame part and/or their removal from said frame part as a single unit.

7. The frame part according to claim 6, wherein said several elements are the collecting surfaces of at least two different stages.

8. The frame part according to claim 6, wherein said several elements are the nozzle parts used for cleaning the impactor stages.

9. A combination element to be used in an electrical impactor which impactor comprises a frame part enclosing at least two impactor stages, wherein each of the stages comprises at least one element, wherein said combination element comprises:
   at least one supporting means,
   at least two elements each having one of the supporting means coupled thereto,
   a connecting element having one of the supporting means coupled thereto,
   wherein said at least two elements belonging to at least two stages can be introduced in and/or removed from said impactor stages arranged in the frame part as a single unit.

10. The combination element according to claim 9, wherein said element is a collecting surface.

11. The combination element according to claim 9, wherein said element is a nozzle part used for cleaning the impactor.

12. The combination element according to claim 9, wherein said element comprises outlets for funnelling a cleaning agent to the impactor stage.

13. The combination element according to claim 12, wherein said cleaning agent comprises hot water vapor.

14. The combination element according to claim 9, wherein said connecting element comprises at least one coupling unit.

15. The combination element according to claim 14, wherein said at least one coupling unit allows the adjustment of a single element without affecting the other elements coupled to said connecting element.

16. The combination element according to claim 15, wherein said coupling unit allows the removal of a single element from said frame part or its insertion in said frame part without affecting the other elements coupled to said connecting element.

* * * * *